United States Patent [19]

Charbonneau

[11] Patent Number: 5,268,214
[45] Date of Patent: Dec. 7, 1993

[54] FRAGRANCE SAMPLER WITH PROTECTIVE TREATMENT

[75] Inventor: Jack W. Charbonneau, Somerset, Wis.

[73] Assignee: Minnesota Mining and Manufacturing, St. Paul, Minn.

[21] Appl. No.: 754,975

[22] Filed: Sep. 4, 1991

[51] Int. Cl.$^5$ .............................................. B32B 9/00
[52] U.S. Cl. .................................... 428/195; 428/40; 428/201; 428/283; 428/537.5; 428/905
[58] Field of Search ............... 428/905, 537.5, 422.2, 428/195, 40, 201, 283

[56] References Cited

U.S. PATENT DOCUMENTS

| | | | |
|---|---|---|---|
| 4,487,801 | 12/1984 | Turnbull et al. | 428/313.5 |
| 4,493,869 | 1/1985 | Sweeny et al. | 428/201 |
| 4,720,417 | 1/1988 | Sweeny et al. | 428/201 |
| 4,769,264 | 9/1988 | Dreger | 428/40 |
| 4,876,136 | 10/1989 | Chang et al. | 428/130 |
| 4,878,775 | 11/1989 | Norbury et al. | 401/132 |
| 4,925,517 | 5/1990 | Charbonneau | 156/176 |
| 4,988,557 | 1/1991 | Charbonneau | 428/204 |
| 4,992,326 | 2/1991 | Dabi | 428/283 |
| 5,093,182 | 3/1992 | Ross | 428/195 |

FOREIGN PATENT DOCUMENTS

| | | |
|---|---|---|
| 0161091 | 11/1985 | European Pat. Off. . |
| 0188883 | 7/1986 | European Pat. Off. . |
| 0189656 | 8/1986 | European Pat. Off. . |
| 0349184 | 1/1990 | European Pat. Off. . |
| 0367581 | 5/1990 | European Pat. Off. . |
| 0441034 | 8/1991 | European Pat. Off. . |

*Primary Examiner*—Patrick J. Ryan
*Assistant Examiner*—Abraham Bahta
*Attorney, Agent, or Firm*—Gary L. Griswold; Walter N. Kirn; Dale A. Bjorkman

[57] ABSTRACT

A sampler for delivery of microencapsulated liquid material has a protective treatment disposed on the substrate sheet overlying ink on the sheet, with microcapsules comprising microencapsulated organic liquid capsule fill disposed on at least a portion of the protective treatment and overlying at least a portion of the ink. The protective treatment is water-stable and organic liquid capsule fill-stable, and is a polymeric solution or emulsion that may be coated on the substrate sheet in a standard coating process in line with the printing of ink on the substrate sheet, and will cure in line to provide the desired protective properties.

9 Claims, No Drawings

5,268,214

FRAGRANCE SAMPLER WITH PROTECTIVE TREATMENT

FIELD OF THE INVENTION

This invention relates to microencapsulated fragrance samplers. More particularly, this invention relates to microencapsulated fragrances bound to a sheet.

BACKGROUND

Fragrance samplers comprising a microencapsulated fragrance and at least one binder layer between two surfaces are well known in the industry. These samplers have become a common vehicle for advertising perfumes and other fragrances through inserts in magazines and the like. Microencapsulated fragrance is typically provided as a laminate on one side of multi-colored, printed paper.

In a market that places a premium on appearance, the samplers of the prior art are deficient in that the area of the advertisement page that bears the microencapsulated fragrance is not printed with ink to match the rest of the device. This is because solvent-containing microcapsules cannot be coated easily onto water-borne inks commonly used in the printing industry. Fragrance microcapsules are usually coated from water-borne slurries that would adversely affect the underlying print quality. When the microcapsules are delivered from an organic solvent slurry, the selection of capsule fill and ink on the paper is limited. For environmental reasons, it is undesirable to deliver the microcapsules from an organic solvent due to the amount of volatile organic components that would be necessarily released. Although organic solvent-borne inks may be substituted for the water-borne inks, problems will occur when the fragrance is actually sampled by the consumer. Specifically, when the consumer applies finger pressure to collect the microcapsules, some of the microcapsules will rupture and release the fragrance oil (the organic liquid fill that is in the capsule, hereinafter, organic liquid capsule fill), which in turn will attack the underlying ink. The ink will then smear on the paper or actually transfer ink to the finger of the consumer. Problems with ink smear may also occur in fragrance samplers having microcapsules that are tightly bound to the paper, so called pull-apart or burst fragrance samplers, because the oils released upon fracture of the microcapsules may attack the ink and cause bleeding even though not physically wiped. Inks may also be adversely affected if there is capsule leakage even without separate wiping. The blank area on the page required to avoid having ink directly under the microcapsules renders a significant portion of the piece unavailable for advertising copy, and also often results in a harsh visual contrast to the overall appearance and graphic design of the advertisement.

U.S. Pat. No. 4,925,517 discloses the use of a base coating on a surface to be subsequently coated with a microcapsule-bearing layer. The base coating functions in part to control the rate and degree of penetration of liquid from the carrier for microcapsules into the underlying paper. Typically the base coating is softened by the carrier liquid of the capsule containing slurry as a means of controlling the bond strength within the sampling device. Preferred polymers to be used in the base coating are water-softenable or organic solvent soluble, as disclosed at column 5, lines 7-15.

U.S. Pat. No. 4,988,557 discloses a similar carrier activated base coating that is applied in a discontinuous pattern to provide separate areas of the sampler in which the capsules are ruptured when the piece is opened, as well as regions in which the microcapsules may be freely removed.

U.S. Pat. No. 4,876,136 to Chang, et. al. discloses a lipstick sampling device that is a three layered structure to deliver a small amount of lipstick to a potential customer. The construction comprises a carrier sheet, a window sheet and a cover sheet. The carrier sheet may be any film or sheet material, and is preferably paper that has an oleophobic impregnate or a barrier layer coated on one side. See column 3, lines 31-37 and column 5, lines 10-32.

U.S. Pat. No. 4,878,775 to Norbury, et. al. discloses a dry liquid applicator that is a support surface with a coating of relatively large microcapsules and with an overlay of a liquid permeable top protective layer. The bottom of the support surface is preferably not readily penetrated by the liquid in the capsules, and is preferably completely impermeable to the liquid. See column 2, lines 27-33. Samples of this construction were offered for sale that had ink printing on the bottom side of the structure, which was only viewable from the underside of the applicator.

SUMMARY OF THE INVENTION

A sampler for delivery of microencapsulated liquid material is provided which comprises a) a substrate sheet;

b) ink disposed on at least a portion of the substrate sheet;

c) a protective treatment disposed on the substrate sheet and overlying at least a portion of the ink, wherein said protective treatment is water-stable and organic liquid capsule fill-stable; and d) microcapsules comprising microencapsulated organic liquid capsule fill disposed on at least a portion of the protective treatment and overlying at least a portion of the ink.

For purposes of this invention, the protective treatment is considered water-stable or organic liquid capsule fill-stable if a piece of ordinary bond paper provided with the protective treatment shows no absorption of liquid into the paper after ten minutes of exposure to a drop of water and to a drop of organic liquid capsule fill placed by an ordinary medicine dropper on the treated side of the paper. The protective treatment is a polymeric solution or emulsion that may be coated on the substrate sheet in a standard coating process in line with the printing of ink on the substrate sheet, and will cure in line to provide the desired protective properties. Preferably, the substrate sheet is paper.

The problems of the prior art are avoided by the use of a protective treatment between the printing inks on the paper and the microcapsule-containing layer or its associated anchoring layers if present. The use of the present protective treatment allows great flexibility in the choice of inks for the device and in the formulation of the microcapsule and binder layer(s) of the sampling device. The present protective treatment allows application of microcapsule slurries or anchoring layers that are cast from water over water-sensitive inks. Similarly, the present invention allows the use of solvent sensitive inks directly under a coating of solvent-containing microcapsules without fear of smearing of the ink when the microcapsules are fractured. In addition to providing a more pleasing visual presentation and preventing unwanted transfer of ink residues with the microcapsules or their contents, the protective treatment of the invention may also reduce the amount of unwanted free fragrance which is released by the device prior to opening by the customer. In some applications, the protective treatment will also serve to reduce or eliminate odors associated with the ink and paper.

DETAILED DESCRIPTION OF THE PRESENTLY PREFERRED EMBODIMENTS

In the description which follows, it will be assumed that the microcapsules contain a fragrance oil. However, it will be appreciated that other microencapsulated liquids may be delivered in the same manner. Examples of such materials include mineral oil microcapsules with associated pigments which have been used in samplers for eyeshadow and other cosmetic materials.

The protective treatment of this invention is selected to be water insoluble after cure, and insoluble in the selected organic liquid capsule fill that is to be used in the particular embodiment to be constructed. This treatment, when applied over commonly employed inks, will allow devices to be constructed which retain the full functionality of the prior art devices, with the additional benefit of permitting the use of graphics under the active microcapsule-bearing regions of the sampler. This protective treatment also finds utility in applications where no underlying ink is present, because the treatment protects the paper from unsightly stains that may occur from the manufacturing process where the paper is exposed to water in the application of the microcapsule/binder slurry, or where the paper is exposed to oil when the microcapsules are broken either during the manufacturing process or by the user.

The protective treatment is a polymeric material that may be coated at rapid web speed from an organic solvent or water, and which forms an effective barrier to oil and water fluids that would deleteriously affect the appearance of the paper. Preferably, the polymer is chemically cross-linked in situ. Alternatively, the polymer may derive its barrier properties from "virtual crosslinks" that are achieved through strong interchain attractive forces such as polymer chain entanglement, ionic interactions, crystallization, van der Walls forces and hydrogen bonding. Entanglement of polymer chains, for example, would likely be observed in block copolymers containing highly phase separated domains. Similarly, polymers containing significant ionic species have strong polar interactions that will provide an effective barrier to liquids, and thus act as a protective treatment under this invention. Chemically crosslinked polymers that are crosslinked in situ are the preferred protective treatment material.

In accordance with this invention, the protective treatment may be applied to a substrate at a high web speed and at very low cost. No additional adhesives or expensive lamination techniques are required to achieve the desired protection.

The protective treatment must be sufficiently transparent or translucent that the ink in the area to be coated with microencapsulated material is ascertainable to the viewer. Preferably, the protective treatment is transparent, so that the underlying ink is not distorted to the naked eye through the treatment layer.

The protective treatment polymer must be cast from an appropriate system that will not damage the image created by the underlying ink. Thus, when the ink is solvent sensitive, the protective treatment must be cast only from solvents that will not dissolve or adversely affect the ink in the time required for the carrier to dissipate. Because most standard and economical press inks are water insoluble, the protective polymer treatment preferably is cast from a water system, either a water solution or emulsion based. Water systems also are advantageous because they do not contain significant quantities of volatile organic components that may have an adverse ecological effect.

Polymers that may be selected for use in the present invention include the polyvinyl alcohols and copolymers thereof, urethanes, acrylated urethanes, acrylate functional acrylate polymers, ethylenically unsaturated monomers, styrene-butadiene polymers; Carboset resins and the like. The above polymers may be rendered suitable for use as a protective treatment in one or more ways. While all of the above polymers may be cross-linked by adding an appropriate crosslinking agent to the solution before application to the paper, alternative curing methods may be utilized as will be now apparent to the skilled artisan. For example, many of the vinylic polymers may be crosslinked by exposure to electron beam or ultraviolet radiation. Alternatively, the readily crystallizable polymers, such as the polyvinyl alcohol polymers or copolymers, may be crystallized by exposure to heat to provide a protective barrier to liquids.

Ionic polymers, such as the Carboset resins commercially available from B. F. Goodrich, Inc. are preferably cast from high pH solutions. As the water evaporates and the pH decreases, the ionic attractions of the polymers promote formation of a protective treatment that is impermeable to water and organic liquid capsule fill.

Crosslinked polyvinyl alcohol is well suited as the protective treatment of this invention as it is both readily applied from aqueous solution and crosslinked by a number of commercially available agents.

Cross-linking agents may be selected from those components known in the art to effect crosslinking of the polymer to make the protective treatment. Examples of such crosslinkers useful for polyvinyl alcohol polymers are dimethylolurea, trimethylolurea, glyoxal, glutaraldehyde, oxalic acid, diepoxides, polyacrolein, dialdhyde starch, divinyl sulfone, diisocyanates, dihydroxydiphenylsulfone, various organometallic compounds such as the titanates commercially available under the KEN-REACT Brand from Kenrich Petrochemicals, Inc., the zirconium analogs to the above titanates, and other bifunctional compounds that react with hydroxyl groups. Cross-linking rate enhancers, such as peroxy catalysts, may also be employed. Similarly, the Carboset resins may be cured by reaction with formaldehyde condensation resins, epoxy resins and multivalent metal ions such as calcium, zinc, iron or aluminum.

The polymer is preferably cross-linked in situ by first adding an effective amount of cross-linking agent to the polymer composition before application to the paper. Preferably, the polymer has a pot life of an hour to a day before application is hampered by cross-linking. The protective treatment may be applied to the paper using any appropriate application method, including, for example, spraying, bar coating, roll coating, extrusion coating, pad coating and curtain coating. The thus treated paper is passed through an oven to speed up the curing process of the protective treatment. Typically, the paper is passed through an oven such that the web temperature is between 200° and 300° F., and more preferably between 225°–250° F. at a web speed of 400–1000 feet/minute.

In use, the cross-linkable polymer is cast on the paper substrate at as low a treatment weight as possible, while still affording the desired amount of protection from liquids. Generally, a treatment weight at least sufficient to avoid having void areas in the protective treatment is required. Treatment weights of between about 0.2 to 0.5 lb/1300 sq ft. are preferred.

The protective treatment of the present invention is particularly useful for fragrance sampling devices that have become prevalent in the advertising industry today. Such sampling devices are applications of a slurry of microcapsules onto paper, typically with a cover sheet of paper adhered to the paper substrate overlying the microcapsules. The cover sheet may be a separate sheet of paper, or may be an extension of the substrate sheet that is folded over to overlie the microcapsules. When the cover sheet is a folded substrate sheet, the cover sheet need not be adhered to the substrate sheet. Such sampling devices may be used as an insert for a magazine or may be actually incorporated into the magazine as a page. Such sampling devices also find usefulness as part of a return envelope for billing purposes, or flyers to be distributed in stores, shopping malls or through the mail.

Fragrance samplers presently are provided in several alternative formats. The first format is where the cover sheet of paper is adhered to the substrate sheet of paper by a binder material provided with the microcapsules. In this format, the microcapsules are strongly bonded to the paper, so that when the cover sheet is removed from the substrate sheet, the microcapsules are ruptured and the fragrance is released. In a second format, the microcapsules are loosely associated with the substrate sheet, and when the cover sheet is removed, the microcapsules are available to be picked up by the user and applied to any location, usually by the finger. In yet another format, the microcapsules are lightly bound to the substrate sheet by a binder material, and may be removed by light finger pressure. An additional format is a combination of one or more of the above, where the user receives an initial burst of fragrance upon removal of the cover sheet and rupture of the bound microcapsules and is still able to pick up microcapsules from the paper to apply to any desired location.

The substrate sheet to be used in the present invention may be any substrate suitable for receiving inks. Preferably, the substrate is paper, and most preferably the substrate is the glossy paper typically used in high quality magazines and advertisements.

The ink to be used in the present invention is preferably a standard printing ink available in the industry. Preferably, the selection of ink is matched with the selection of protective treatment to be used such that the combination has sufficient cohesive and adhesive strength to remain on the paper without splitting off. This is particularly important in the sampler format where the microcapsules are adhered to the substrate and cover sheet, and are ruptured upon removal of the cover sheet. Cohesive or adhesive failure of the underlying ink in this format could result in absolute failure of delivery of the fragrance.

The binder material used for adhering the microcapsules to the substrate paper, or the cover paper to the substrate paper may be any appropriate pressure sensitive, water or solvent soluble, or thermally activatable adhesive. Appropriate materials include polyurethanes, polyacrylates, polyvinyl resins, polyamides, polyesters, polyolefins, gum arabic, gelatin and the like.

In a typical manufacturing operation, the paper is first printed with the ink as desired. The ink is then dried in-line by passing through an oven. Protective treatment is then applied to the paper, and allowed to cure as appropriate for the material selected. Curing may optionally be accelerated by passing the paper through a second oven. Optional anchoring layers for anchoring the microcapsules to the substrate may be applied and dried at this point. Microcapsules are then applied to the paper, preferably in a water-based slurry. A cover sheet is then optionally provided over the microcapsules to protect them from premature rupture. The cover sheet may be a separate paper, or may be provided by folding over of the substrate sheet to overlie the microcapsules. It has been found that an additional drying step is not usually required at this stage to prepare a satisfactory product. The carrier liquid for the microcapsules has been found to dissipate effectively from the product even with the cover sheet in place and product stacked for later packaging.

The following examples are provided for purposes of illustration only, and are not intended to be limiting of the scope of the invention in any way.

EXAMPLE 1

In the following example, the fragrance oil (Giorgio Red) was encapsulated by the process described in Example 20 of U.S. Pat. No. 3,516,941. The resulting capsules had a mean diameter of about 20 micrometers and an estimated payload of 85% by volume (ratio of oil to total capsule volume.) The microcapsules were washed with cold tap water, filtered, and reslurried to 40.6% solids.

| Component | Dry Weight | Wet Weight |
| --- | --- | --- |
| Microcapsules (40.6% solids) | 1206.4 | 2971.4 |
| Klucel MF (added as a 3% predissolved solution) | 6.5 | 215.1 |
| Superpearl (pearlescent pigment obtained from Flamenco) | 77.4 | 77.4 |

The slurry was thoroughly mixed and passed through a 125 micron screen to remove large particles or agglomerates.

The protective treatment solution was prepared by predissolving the Vinol 523 in water to 14% solids. The glyoxal and ammonium chloride were added just prior to coating.

| Component | Dry Weight | Wet Weight |
| --- | --- | --- |
| Vinol 523 polyvinyl alcohol | 283.68 | 2026.30 |
| Glyoxal | 34.18 | 85.44 |
| Ammonium chloride | 14.27 | 14.27 |
|  | 332.13 | 2126.01 |
| Water |  | 890.26 |
|  | 332.13 | 3016.27 |

Samplers were produced at Japs Olson Printing Co. on their M-80-5 Harris heat set web off-set printing press at a speed of 200 feet per minute. The Warrenflo 70 pound C2S paper was printed and dried in the first oven. The PVA treatment described above was applied over the printing just prior to a second oven at a variety of treatment weights from 0.24 to 0.48 pounds per 1300 square feet. The treatment was dried and crosslinked at a web temperature of 235° F. The microcapsule/pigment slurry was then coated over the crosslinked polyvinyl alcohol at 3.5 pounds per 1300 square feet. The paper was folded so that a portion of the paper covered the microcapsules and allowed to dry at ambient conditions for 72 hours. After drying, the microcapsules could easily be removed for application to the skin by rubbing with a finger tip. The ink could not be smeared even with prolonged rubbing to rupture capsules over the protected area.

What is claimed is:

1. A sampler for delivery of microencapsulated liquid material comprising
   a) a substrate sheet;
   b) ink disposed on at least a portion of the substrate sheet;
   c) a protective treatment disposed on the substrate sheet and overlying at least a portion of the ink, wherein said protective treatment is water-stable and organic liquid capsule fill-stable; and
   d) microcapsules comprising microencapsulated organic liquid capsule fill disposed on at least a portion of the protective treatment and overlying at least a portion of the ink.

2. A sampler according to claim 1, wherein said substrate sheet is paper.

3. A sampler according to claim 1, wherein said protective treatment is a crosslinked polymer.

4. A sampler according to claim 1, further comprising a cover sheet over said microcapsules.

5. A sampler according to claim 4, wherein said cover sheet is paper.

6. A sampler according to claim 1, wherein said microcapsules are adhered to said protective treatment by a binder material.

7. A sampler according to claim 1, wherein said protective treatment is provided at a treatment weight between 0.2 lb/1300 sq. ft. and 4 lb/1300 sq. ft.

8. A sampler according to claim 1, wherein said protective treatment is a crosslinked polyvinyl alcohol polymer.

9. A sampler according to claim 1, wherein said organic liquid capsule fill is a fragrance oil.

* * * * *